(12) United States Patent
Piccardi et al.

(10) Patent No.: US 7,473,434 B2
(45) Date of Patent: Jan. 6, 2009

(54) MACA EXTRACT AND COSMETIC COMPOSITION CONTAINING SUCH AN EXTRACT

(75) Inventors: Nathalie Piccardi, Arceau (FR); Antoine Piccirilli, Versailles (FR); Philippe Msika, Versailles (FR); François Paul, Toulouse (FR)

(73) Assignee: Laboratoires Expanscience, Courbevoie (FR)

( * ) Notice: Subject to any disclaimer, the term of this patent is extended or adjusted under 35 U.S.C. 154(b) by 238 days.

(21) Appl. No.: 10/561,271

(22) PCT Filed: Jun. 17, 2004

(86) PCT No.: PCT/FR2004/001505

§ 371 (c)(1), (2), (4) Date: Dec. 19, 2005

(87) PCT Pub. No.: WO2004/112742

PCT Pub. Date: Dec. 29, 2004

(65) Prior Publication Data

US 2007/0098823 A1    May 3, 2007

(30) Foreign Application Priority Data

Jun. 19, 2003  (FR)  .................... 03 07388

(51) Int. Cl.
*A01N 65/00*  (2006.01)
(52) U.S. Cl. ..................................... 424/725
(58) Field of Classification Search ........................ None
See application file for complete search history.

(56) References Cited

FOREIGN PATENT DOCUMENTS

| FR | 2 778 565 A | 11/1999 |
|---|---|---|
| FR | 2 802 418 A | 6/2001 |
| GB | 2 011 910 A | 7/1979 |
| JP | 08012565 * | 1/1996 |
| JP | 2000-319120 A | 11/2000 |
| JP | 2001-39854 | 2/2001 |
| JP | 2001-039854 A | 2/2001 |
| JP | 2003-155213 | 5/2003 |
| JP | 2003-155213 A | 5/2003 |
| WO | WO-03/064669 A1 | 8/2003 |

OTHER PUBLICATIONS

"Protein," Wikipedia (http://en.wikipedia.org/wiki/Protein).
Comas et al., "Estudio Bromatologico de la Maca o Paca (Lepidium Meyenii)." Alimentaria, Oct. 1997, pp. 85-90.
Parrado et al., "Production of Soluble Enzymatic Protein Hydrolysate From Industrially Defatted Nondehulled Sunflower Meal," Journal of Agricultural and Food Chemistry, American Chemical Society, vol. 39, No. 3, Mar. 1, 1991, pp. 447-450.
"Hydrolysis"; Merriam-Webster Dictionary (http://www.merriam-webster.com/dictionary/hydrolysis).
Bergmann et al.; "The role of Specificity in the Enzymatic Synthesis of Proteins"; The Journal of Biological Chemistry; 1937, pp. 707-720.
"Papain", 2008 Sigma-Aldrich Co.; Enzyme Explorer, "Papain" entry, E.C. 3.4.22.2.

\* cited by examiner

*Primary Examiner*—Michael V Meller
(74) *Attorney, Agent, or Firm*—Foley & Lardner LLP

(57) ABSTRACT

The invention relates to a method for extracting substances from maca, to the obtained extract, to a cosmetic and pharmaceutical composition containing said extract, and to the use thereof as an anti-aging cosmetic agent. The method is characterized by a step involving the use of an enzymatic hydrolysis of proteins.

20 Claims, 4 Drawing Sheets

A) "Young" fibroblasts

B) « Aged » fibroblasts

MACA EXTRACT AND COSMETIC COMPOSITION CONTAINING SUCH AN EXTRACT

The invention concerns a method for extracting maca, the extract obtained, a cosmetic composition containing the same and its use as an anti-age cosmetic agent.

The botanical name of maca is *Lepidium meyenii Walp*. Among its vernacular names the English names may also be cited of: maca, Peruvian ginseng, quechua; in Spanish: maca, maka, maca-maca and in Quechua: ayak chichica, ayak willku, maka. It belongs to the Brassicaceae (Cruciferae) family of Tribe Lepidieae.

Maca is a small herbaceous plant 12 to 20 cm high. Its underground part measures 2 to 5 cm. It comprises a tap root surmounted by the lower part of a widened, fleshy hypocotyl. In the dry state the whole is reminiscent of the shape of a turnip. To simplify, the part of the plant below the ground forming the fraction that is used will be called "tuber".

The leaves form a rosette and are new renewed from the centre. The small flowers are autogamous. The fruit is a small silique (4 to 5 mm) with two valves each containing a seed.

Maca and other botanically close wild Lepidieae have been located up until now in a few mountainous regions of the Andes cordillera (Peru, Bolivia, Ecuador). These plants are able to withstand frosts even during their growth period. Long considered as "short day" plants on account of their habitat, work on their photoperiod response has shown that their growth is similar whether under long or short day conditions.

The plant behaves likes an annual when climatic conditions are favourable (sufficiently moist soil and temperate temperature). Its vegetative cycle is then 11 months. It becomes biennial under high mountain climates maintaining its underground part dormant during the dry season.

Maca was probably "domesticated" in San Blas, Peru, 1300 to 2000 years ago. Since then, its cultivation has always been confined to the central mountains of Peru at an altitude of between 3500 and 4000 in the Departments of Junin and Pasco. The largest cultivation areas are concentrated around Lake Junin. Formerly they were less restrictive, extending as far as Cusco and Lake Titicaca. In these regions the low temperatures and strong winds greatly restrict the growing of other crops with the exception of potatoes.

Maca is currently cultivated in small plots of 500 sq.m. following very traditional methods. The seeds are sown early in the rain season in September-October. The tubers are usually harvested 8 to 10 months after sowing. Harvesting begins in May-June. When harvested the tubers are left to dry in the sun for 6 to 15 days. They are then stored away from light and humidity until use. The tubers keep well.

Chief analysis results of the chemical composition of maca were published by Dini et al in 1994 (Dini A., Migliuolo G., Rastrelli L., Saturnino P., Schettino O, Chemical composition of *Lepidium meyenii*. Food chemistry, 1994, 49, 4, pp. 347-349 (Eng) then by Comas et al in 1997 (Comas M., Miquel X., Arias G., de la Torre M. C. Bromatological STudies on *Lepidium meyenii*. Alimentaria (Madrid), 1997, 286, pp. 85-90 (Spanish):

humidity: 10 to 20%
mineral materials of most interest (mg/100 g):
  Potassium 1150 to 2050
  Calcium 150 to 260
  Iron 3 to 16
  Copper 0.2 to 6
  Zinc 1.5 to 6
  Aluminium 3 to 7

Carbohydrates: 60 to 65%
  Starch 30 to 35%
  Saccharose 3 to 20%
  Fructose 8 to 10%
Glucose: 3 to 7%
Fibres: 4 to 8%
Proteins: 10 to 14%
Lipids: 0.5 to 2%

Maca is traditionally used as food, but also for its therapeutic properties.

The nutritional value of maca, close to that of cereals traditionally eaten, is in fact a food of choice and major interest for the populations living on the high Peruvian plateaux.

The tuber of the maca has had popular use for hundreds of years for medicinal purposes, to increase fertility in man and animals (Leon J., The maca (*Lepidium meyenii*), a little-known food plant of Peru. Economic botany, 1964, 18, 2 pp. 122-127 [English]).

The Kallawaya, travelling healers in the Andes, prescribed the fresh tuber cut into fine slices, in decoction, three or four days after the last menstrual period for sterile women wishing to become pregnant (Girault L. *Kallawaya*. Guérisseurs itinérants des Andes. ORSTOM éd., Paris, 1984, pp. 218-219 [French]).

At the present time the popularity of maca is on the increase on account of the stimulating and aphrodisiac properties it is purported to have. The maca tuber has been related to ginseng, Panax ginseng, (to excess on account of a promising potential market), hence its name of Peruvian ginseng.

Other uses of the tuber include its benefit in respiratory disorders (tuberculosis), chronic fatigue, memory disorders, menopausal symptoms, as a course of treatment for attacks of rheumatism, etc.

The purpose of the present invention is to propose a maca extract permitting stimulation of the metabolism and proliferation of fibroblasts to prevent and/or fight against chronological, extrinsic (sun, tobacco, pollution, stress) and menopausal skin ageing.

Skin ageing is characterized in particular by a reduction in the number and activity of fibroblasts.

Raw maca, generally in the form of a dehydrated powder, is almost insoluble in water. On this account, its use in cosmetic care products is difficult to consider as such. Also, the bioavailability of the constituent molecules of the plant (mineral salts, carbohydrates, proteins, vitamins, . . . ) is almost non-existent by cutaneous route.

Therefore the invention concerns a fully hydrosoluble peptide extract of maca, its method of preparation, cosmetic compositions containing the same and their use as anti-ageing active agent.

Figure 1:
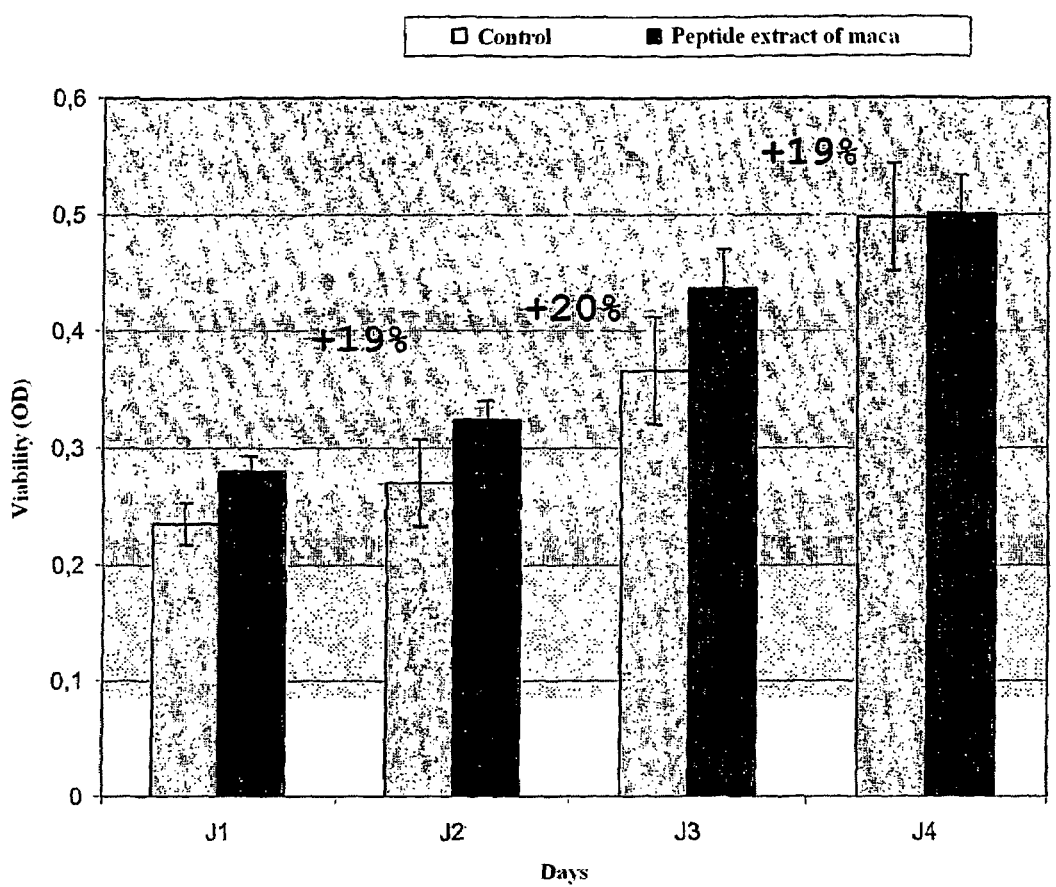
FIG. 1 illustrates the viability of the cells cultured in the absence (control) or presence of maca peptide extract.

The peptide extract can be liquid or solid depending on whether or not the extract has been freeze-dried during the second step of its preparation.

Skin ageing may evidence itself in particular through collapse of the tissues, translating especially as loss of skin tonicity and firmness, a reduction in skin thickness and elasticity, the onset of senescence pigment blemishes, loss of skin radiance and uniformity or further by the onset of wrinkles or fine lines.

More particularly, the subject of the invention is a method for preparing an aqueous peptide extract of maca, characterized in that it is conducted using a powder of ground maca tubers, in that it comprises at least one enzymatic hydrolysis step of the proteins.

Hydrolysis is preferably enzymatic. Enzymatic hydrolysis may be particularly conducted with an amylase and protease mixture. Preferably, the amylase/protease ratio ranges from 50/50 to 90/10, preferably from 75/25 to 85/15 to convert the protein fraction of the plant into hydrosoluble peptides.

The aqueous extract thus obtained may then be concentrated to remove insolubles such as fibres.

According to one variant of the inventive method, the aqueous extract may then be purified by ultrafiltration to extract any traces of residual proteins. In this case, advantageously a cut-off threshold of 10 kD is chosen to retain those peptides having a molecular weight of less than 10 kD.

Therefore, according to a preferred variant of the invention, the method comprises the following steps:
  washing then drying maca tubers in a stream of hot air (for example at 60° C.),
  grinding the maca tubers into a fine powder,
  suspending the powder in water, advantageously at between 1 and 25% by weight,
  hydrolysing the proteins in the presence of a protease and amylase, for example in a ratio of 80/20,
  centrifuging to remove insolubles (fibres),
  ultra-filtrating the solution (advantageously cut-off threshold of 10 kD),
  optionally followed by a concentration step into dry matter by diafiltration (advantageously 100 Da) and/or a controlled evaporation step and finally, optionally followed by a sterilizing filtration step (preferably on a 0.2 μm filter).

A further subject of the invention is an aqueous peptide extract of maca able to obtained by the above-described method in all its variants.

This aqueous peptide extract of maca advantageously has a dry matter content of between 1 and 300 g/l, preferably between 2 and 10 g/l.

With respect to the dry matter, the content of reducing sugars may lie between 2 and 70% and preferably between 35 and 45%. By reducing sugars is meant reagent sugars: they are capable of giving electrons to a molecule. Glucose, fructose and maltose may be cited. Historically, this term is derived from the discovery by Fehling in the XIX century who proved that some sugars react with cupric ions to convert them into cuprous ions. Visually, this so-called "reduction" action is seen as a change in colour of Fehling's solution: initially blue, it turns to brick red in the presence of reducing sugars.

The pH of a solution with 20 g/l dry matter may lie between 5 and 8, preferably between 6 and 7.

A further subject of the invention is a method for preparing a solid peptide extract of maca, characterized in that the aqueous peptide extract, optionally concentrated and/or sterilized, is freeze-dried. In other words a solid powder is obtained (dry extract) which has the particular advantage of being hydrosoluble, which is not the case with original maca tuber powder.

A further subject of the invention is a solid peptide extract of maca able to be obtained with the above-described method.

This solid peptide extract of maca may also be characterized by its alpha amino nitrogen content. This may lie between 2 and 70.

Preferably, the solid peptide extract of maca of the invention has the following amino acid composition (in weight percentage with respect to the total weight of amino acids):

| | |
|---|---|
| Alanine | 5-9% |
| Arginine | 15-20% |
| Aspartic acid | 8-12% |
| Cystine-cysteine | <2% |
| Glutamic acid | 9-15% |
| Glycine | 3-7% |
| Histidine | 1-6% |
| Isoleucine | 2-7% |
| Leucine | 4-9% |
| Lysine | 3-7% |
| Methionine | 1-5% |
| Phenylalanine | 4.9% |
| Proline | <1% |
| Serine | 2-8% |
| Threonine | 1-7% |
| Tyrosine | 1-7% |
| Valine | 4-10% |
| Tryptophane | <0.5% |

A further subject of the invention is a cosmetic composition characterized in that it contains an aqueous or solid peptide extract of maca such as previously described and at least one cosmetically acceptable excipient.

Said cosmetic composition may be particularly intended to combat skin ageing.

A further subject of the invention is therefore a cosmetic treatment method comprising the application of said composition onto the skin surface of an individual.

Finally the subject of the invention is the use of an aqueous or solid peptide extract of the invention as anti-ageing active agent. More particularly, this aqueous or solid extract may be used to stimulate cell metabolism, namely mitochondrial activity in particular of the dermal fibroblasts. Also this aqueous or solid extract may be used to stimulate cell energy. By "cell energy" is meant the energy reservoir on which the cell draws to perform all its vital activities (in particular mitosis, growth, synthesis of macromolecules, DNA repair). Finally, it may be used to combat external aggressions of sun, tobacco, pollution or stress type.

The invention is illustrated below with the described examples of embodiment.

EXAMPLE 1

Preparation of the Extract 10 kg of maca powder are dispersed in 80 litres of demineralised water in the presence of 0.25 kg amylase. The mixture is maintained at 50° C. for 5 hours at a constant pH of 5.

During a second step, 0.25 kg of Alcalase® protease marketed by Novo Nordisk are added. The mixture is then maintained at 60° C. for 1 hour, at a constant pH of 8.

The hydrolytic enzymes are then denatured by heating to 90° C. for 20 minutes.

The mixture is centrifuged at 5550 rpm in the presence of a filtering clay adjuvant and filtered through 1 μm cloth for clarification.

The collected solution is ultra-filtrated (cut-off threshold 10 kD), the filtrate is concentrated by diafiltration (10 Da) down to a content of 10% dry matter and then sterile filtered (0.2 µm).

The extract obtained has the following characteristics:

| | |
|---|---|
| Appearance/Colour | Clear solution of yellow colour |
| Smell | Characteristic |
| Dry matter (w/w) | 10.4% |
| pH in 20 g/l solution | 6.8 |
| Absorbance | 0.530 to 420 nm |
| | 0.093 to 550 nm |
| Composition with respect to dry matter (w/w) | |
| Alpha amino nitrogen | 4% |
| Total nitrogen | 1.7% |
| Reducing sugars | 42% |

HPLC profile of the hydrolysate of maca powder—Molecular weight distribution:

| HPLC peak | Mean molecular weight (g/mol) | Relative % |
|---|---|---|
| 1 | 1170 | 38.9 |
| 2 | 360 | 29.3 |
| 3 | 180 | 16.2 |
| 4 | 41 | 15.6 |

EXAMPLE 2

Biological Activity 2-1 Effect on Normal Human Fibroblasts

Material and Method

Cell: model of normal human fibroblasts, mono layer culture.

Treatment: the cells are cultured in the absence (control) or presence of 0.1% of the peptide extract obtained in example 1.

Evaluation of cell metabolism: The effect of this extract was assessed by measuring the mitochondrial activity (MTT test i.e 3-(4,5-dimethylthiazole-2-yl)-2,5-diphenyl tetrazolium bromide) every day for one week.

Results:

On average the peptide extract of maca at a dose of 0.1% stimulated the metabolism of the dermal fibroblasts by 20% with respect to the non-treated control cells. FIG. 1 illustrates the viability of the cells cultured in the absence (control) or presence of maca peptide extract.

Conclusion

The peptide extract of maca enables stimulation of the cell metabolism of dermal fibroblasts.

2-2 Effect on Human Fibroblasts Artificially Aged in Vitro

Study Model

For this study we used a model of skin fibroblasts artificially aged in vitro, characterized by the use of fibroblasts derived from plastic surgery (female aged 26 years) and cultured to high passage numbers >p15. With each passage, or doubling of population, the fibroblasts:

a) changed appearance and became more widespread b) multiplied much slower compared with the same fibroblasts used with <p5 passages and considered "young"

Figure 2:
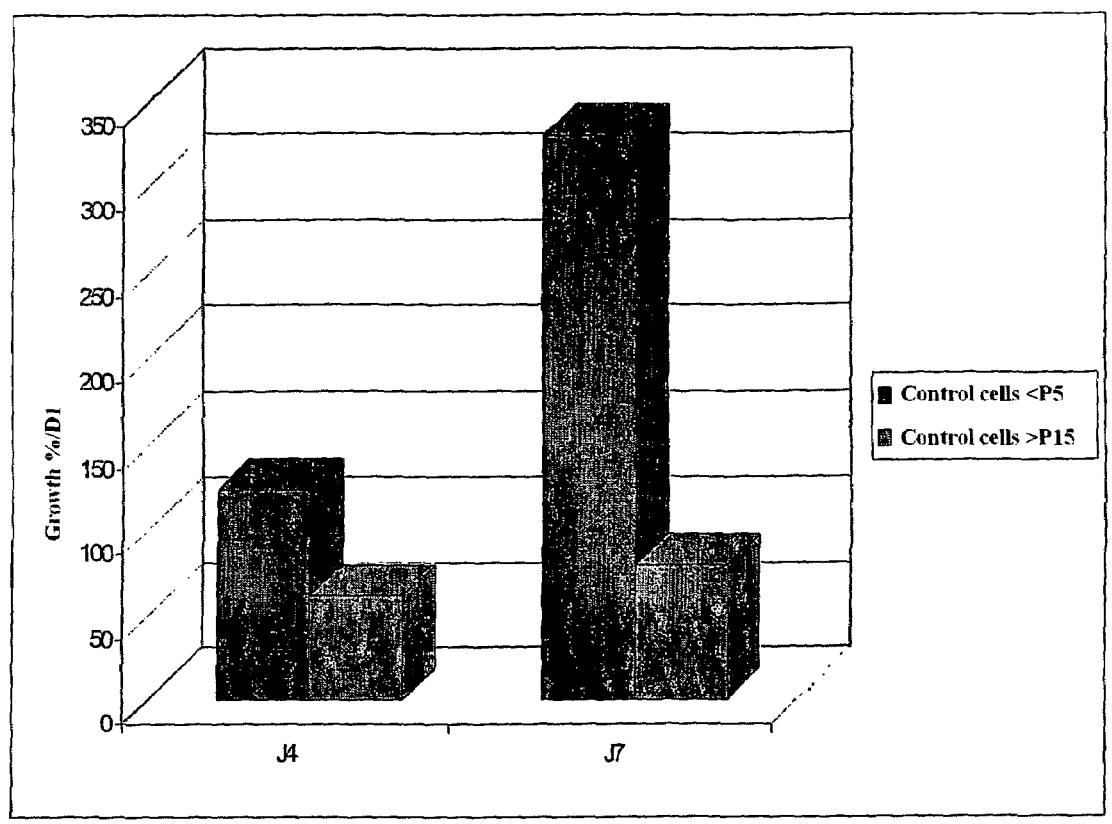
FIG. 2 illustrates the comparison between replication capacities (division) of "young" fibroblasts (<p5) and aged fibroblasts (>p 15).

(FIG. 2 illustrates the comparison between replication capacities (division) of "young" fibroblasts (<p5) and aged fibroblasts (>p15)).

Artificial ageing in vitro or the phenomenon of replicate senescence was evidenced by Leonard Hayflick in 1961 (Hayflick L and Moorhead PS. The serial cultivation of human diploid cell strains. Exp Cell Res, 25: 585-621 1961). Initially Hayflock showed that the cell can only divide a limited number of times when placed in culture, then described the possible connection between replicate senescence and cell ageing (Hayflick L. The limited lifetime of human diploid cell strains. Exp Cell Res., 37). Cells apparently have an inner clock influencing or directly limiting their dividing capacity. This programmed stoppage of cell division could be related to the loss of telomers (chromosome ends). An acceptable correspondence between in vivo (loss of approximately 50 base pairs/cell doubling) and in vitro (loss of approximately 70 base pairs/cell doubling) tends to show that the in vitro cell division model prefigures the occurrence in vivo.

Results

The cells were cultured for 7 days in the presence or absence of maca peptide extract at a dose of 0.01%. Cell viability was measured using the MTT test. The results are expressed as growth %/first day of culture (d1) as per the formulation: [OD dX−OD d1/OD D1]×100, where OD=optical density measured at 570 nm; d=day of culture.

Figure 3A:
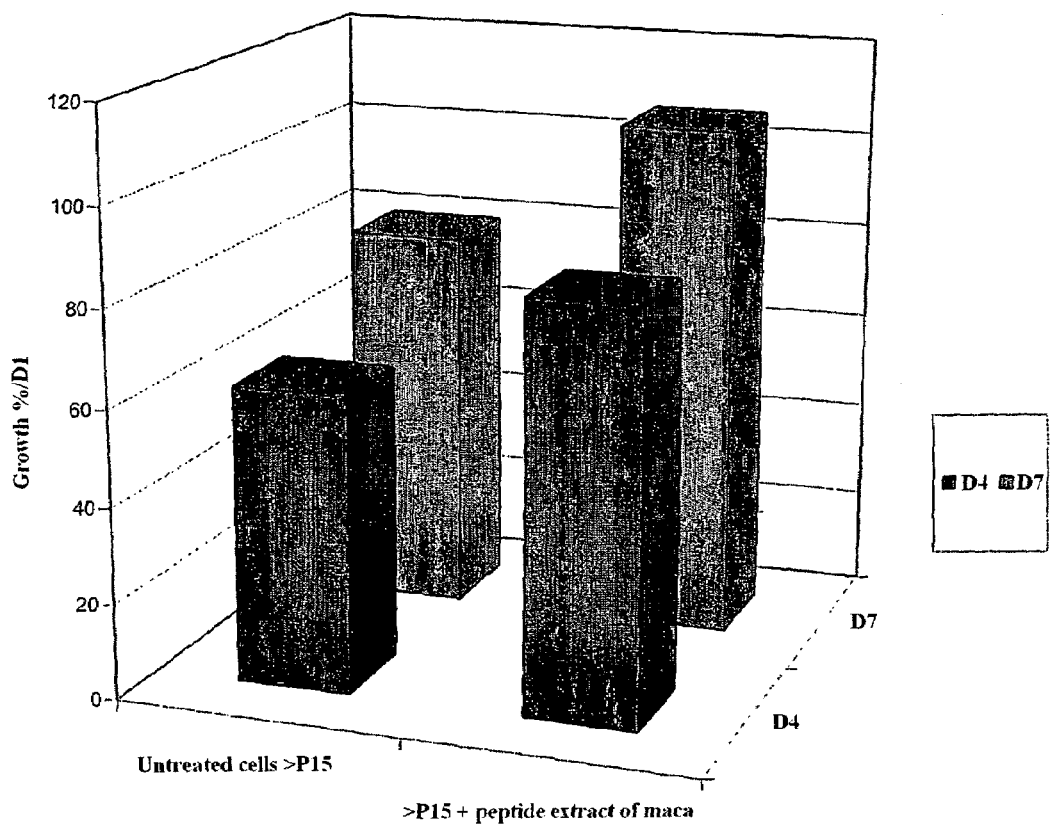
FIG. 3A shows that the dividing capacities of "young" fibroblasts can be increased.
Figure 3B:
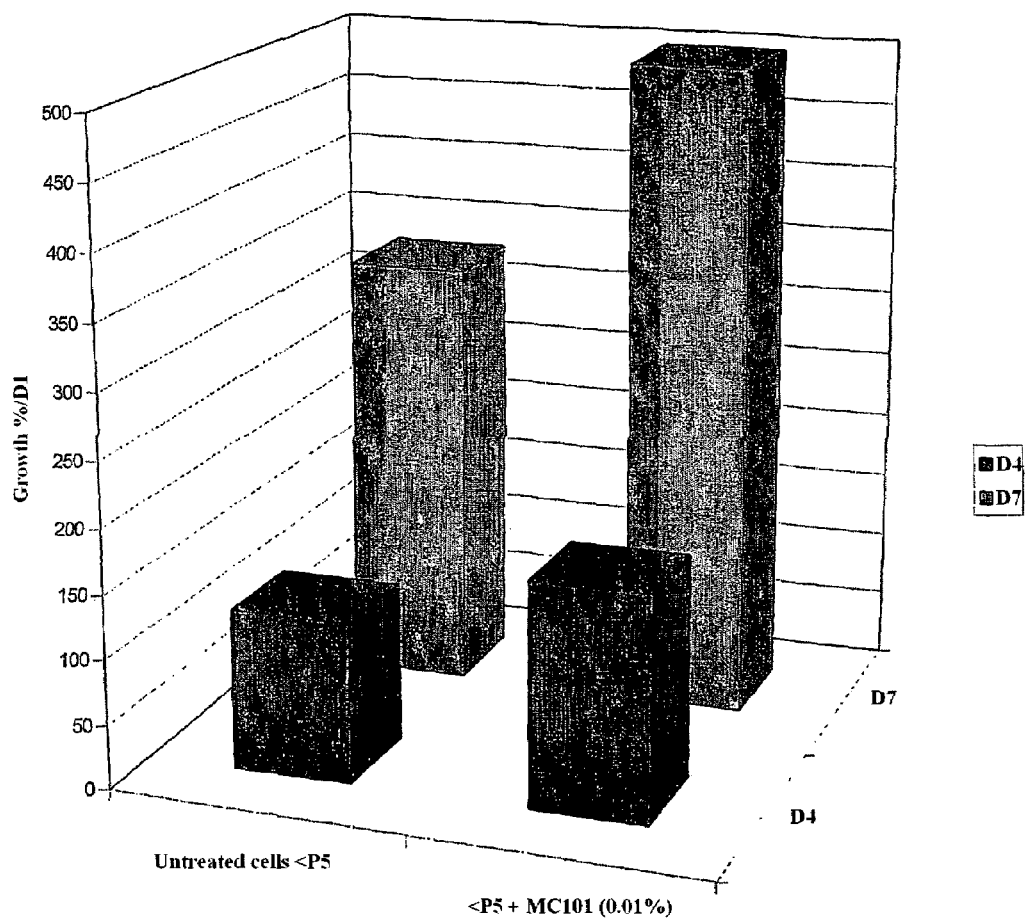
FIG. 3B shows that the dividing capacities of "aged" fibroblasts can be increased.

Under these experimental conditions, the hydrolysate of maca, at a dose of 0.01%, makes it possible to increase the dividing capacities of "young" fibroblasts (passages<5) by +35 and 40% respectively at d4 and d7 (FIG. 3A) and "aged" fibroblasts (>p15) by +26 and 29% respectively at d4 and d7 (FIG. 3B). FIGS. 3A and 3B are appended hereto.

Conclusion

The hydrolysate of maca, by stimulating the proliferating capacities of "aged" fibroblasts may therefore compensate for the age-related decrease in dermal cell population, and may therefore oppose intrinsic skin ageing.

2-3 Effect on the Production of Lipid Peroxides in Human Cells

The purpose of the study is to evaluate the effects of the maca peptide extract on the lipid peroxidation rate (LP) in human cells (Jurkat) exposed or not to UVA+UVB radiation. LP measurement was made with a specific fluorescent probe by flow cytometry. This method has the advantage of showing great sensitivity when measuring the fluorescence of individual cells, over a large number of cells (10 000 cells analysed per sample).

Materials & Methods

The cells used are Jurkat human lymphoid cells distributed in 24-well plates with $8.10^5$ cells/well.

The culture medium is RPMI 1640 (Invitrogen 31870-025) at 37°C and in the presence of 5% $CO_2$.

The test medium is MEM without phenol red and without calf serum (Polylabo 5503401).

Tests are conducted with the peptide extract obtained in example 1, with twofold dilution i.e. in the form of an extract with 5% dry matter. A solution $S_1$ containing 2% of this extract is prepared in the test medium.

The control used is butyl hydroxyanisol (BHA Sigma ref. B 1253) in a 50 µM solution in absolute ethanol. Tests are conducted with a solution $S_2$ containing 100 µM BHA prepared in the test medium.

The fluorescent probe is 5-N-dodecanoyl-amino-fluoresceine (Free. Rad. Biol. Med., 1997, 22, 13-100) in a 5 µM solution in absolute ethanol. The tests are conducted using a 1 µM probe solution $S_3$ prepared in the test medium.

The human cells are pre-incubated in the culture medium, then washed in the test medium. They are subsequently incubated in the presence of the $S_1$ solution of the peptide extract or the $S_2$ control solution. The probe solution $S_3$ is added to each batch for LP assay.

After 45 minutes incubation, the fluorescent probe is removed by washing in the test medium.

Part of the batches are then irradiated with UVB, another part without irradiation used as control.

After 20 minutes incubation the fluorescence parameters are measured by flow cytometry.

Determination of the relative quantity of lipid peroxides (LP) is based on measurement of the reduction in fluorescence of the probe integrated in the cell membranes. An increase in the fluorescence signal translates a reduction in the basal rate of membrane lipid peroxides.

The studies are conducted in triplicate.

Results

The results obtained are expressed as the value of fluorescence intensity, and percentages with respect to the control are calculated using the values of fluorescence intensity.

The results obtained are grouped together in the following tables:

Relative Intercellular Quantity of Lipid Peroxides (LP)

| Treatment | Fluorescence intensity | Mean | Sd | 1/fluorescence intensity | % control +UV |
|---|---|---|---|---|---|
| Control C11/fluor | 1.16 1019 1019 | 1.18 | 0.02 | — | — |
| Control −UV | 530.21 463.66 525.39 | 506.42 | 37.11 | 0.00197 | 37 |
| Test +UV | 198.83 172.38 186.04 | 186.42 | 13.30 | 0.00536 | 100 |
| BHA 100 µM | 362.40 368.20 393.42 | 374.67 | 16.49 | 0.00267 | 50 |
| 2% solution of extract in example 1 | 254.23 252.27 239.47 | 248.66 | 8.02 | 0.00402 | 75 |

$P < 0.01$

Relative Intracellular Quantity of Lipid Peroxides (LP) Without UV

| Treatment | Fluorescence intensity n = 10000 cells) | Mean | sd | 1/fluorescence intensity | % control +UV |
|---|---|---|---|---|---|
| Control - C11/fluor | 1.50 1.24 1.26 | 1.33 | 0.14 | — | — |
| Control - UV | 530.21 463.66 525.39 | 506 | 37.11 | 0.00197 | 100 |
| BHA 100 µM | 741.05 745.64 770.93 | 753 | 16.09 | 0.00133 | 67 |
| 2% MC101 | 716.73 682.84 716.34 | 705 | 19.45 | 0.00142 | 72 |

$P < 0.01$

Irradiation has been significantly reduced. The fluorescence intensity of the probe translates as the presence of radical reactions at the cell membranes, and hence an increase in LP quantity.

The reference antioxidant BHA tested at 100 µM significantly inhibited loss of fluorescence showing 50% irradiation with respect to the control in the presence of UV.

The peptide extract of the invention significantly reduced the quantity of lipid peroxides both in the absence of UV (72% reduction compared with the control) and in the presence of UV (75% reduction with respect to the control).

Conclusion

By preventing the formation of free radicals, the peptide extract of maca makes it possible to counter one of the major factors of skin ageing consisting of the formation of reactive oxygenated species.

EXAMPLE 3

Example of a Cosmetic Formulation for Anti-age Cream

| Anti-age cream | |
|---|---|
| Aqua | QSP 100 |
| Isononyl Isononancate | 7.00 |
| Di-C12-13 Alkyl Malate | 7.00 |
| Isocetyl Stearate | 5.00 |
| Butylene Glycol | 3.00 |
| Aqueous peptide extract of maca prepared as in example 1 | 2.00 |
| Dicaprylyl Ether | 2.00 |
| Silanediol Salicylate | 2.00 |
| Arachidyl Alcohol | 1.65 |
| Tromethamine | 1.18 |
| Cetyl Alcohol | 1.00 |
| Glycine | 1.00 |
| Tocopheryl Acetate | 1.00 |
| Behenyl Alcohol | 0.90 |
| Squalane | 0.79 |
| Sodium Citrate | 0.66 |
| PPG-12/SMDI Copolymer | 0.50 |
| Arachidyl Glucoside | 0.45 |
| Perfume | 0.40 |
| Sclerotium Gum | 0.16 |
| Ceteartyl Alcohol | 0.13 |
| Citric Acid | 0.11 |
| Sepigel 305* | 0.10 |
| Preserving agent | QS |

*product marketed by Seppic

The invention claimed is:

1. Method for preparing an aqueous peptide extract of maca, comprising hydrolyzing proteins of a powder of ground maca tubers in the presence of water, protease and amylase to form an aqueous peptide extract, and purifying the aqueous peptide extract by ultrafiltration.

2. Method for preparing the extract of claim 1, wherein the amylase/protease are used in a ratio ranging from 50/50 to 90/10.

3. Method of claim 1, wherein the aqueous extract is then concentrated to remove insolubles.

4. Method of claim 1, wherein the ultrafiltration has a cut-off threshold of 10 kD.

5. Aqueous peptide extract of maca obtained using a method comprising hydrolyzing proteins of a powder of maca tubers in the presence of water, protease and amylase to form an aqueous peptide extract and purifying the aqueous peptide extract by ultrafiltration.

6. Aqueous peptide extract of claim 5, having a dry matter content between 1 and 300 g/l.

7. Method for preparing a solid peptide extract of maca, comprising:
   a) hydrolyzing proteins of a powder of maca tubers in the presence of water, protease, and amylase to form an aqueous peptide extract;
   b) purifying the aqueous peptide extract by ultrafiltration to form a purified aqueous peptide extract;
   c) optionally concentrating and/or sterilizing the purified aqueous peptide extract; and
   d) freeze-drying the purified aqueous peptide extract.

8. Solid peptide extract of maca obtained using the method as in claim 7.

9. Solid peptide extract of maca as in claim 8, wherein the content of alpha amino nitrogen lies between 2 and 70%.

10. Solid peptide extract of maca as in claim 8, wherein the amino acid composition is of the following weight percentage with respect to the total weight of the amino acids of the composition.

| | |
|---|---|
| Alanine | 5-9% |
| Arginine | 15-20% |
| Aspartic acid | 8-12% |
| Cystine-cysteine | <2% |
| Glutamic acid | 9-15% |
| Glycine | 3-7% |
| Histidine | 1-6% |
| Isoleucine | 2-7% |
| Leucine | 4-9% |
| Lysine | 3-7% |
| Methionine | 1-5% |
| Phenylalanine | 4.9% |
| Proline | <1% |
| Serine | 2-8% |
| Threonine | 1-7% |
| Tyrosine | 1-7% |
| Valine | 4-10% |
| Tryptophane | <0.5%. |

11. Peptide extract of maca of claim 5, which can be used to stimulate the proliferation and growth of skin cells and more particularly of fibroblasts.

12. Peptide extract of maca of claim 5, which can be used to stimulate the mitochondrial activity of skin cells and more particularly of the fibroblasts.

13. Cosmetic composition comprising the peptide extract of meca of claim 5, and at least one cosmetically acceptable excipient.

14. A method of combating skin aging, consisting of applying to skin the composition of claim 13.

15. A method of combating outside aggressions selected from the group consisting of sun, tobacco, pollution, and stress consisting of applying to skin the composition of claim 13.

16. A method of combating loss of tonicity and/or elasticity of the skin and/or to the onset of senescence pigment blemishes comprising administering the extract of claim 5.

17. A cosmetic composition comprising the peptide extract of meca of claim 8 and at least one cosmetically acceptable excipient.

18. A method of combating the loss of tonicity and/or elasticity of the skin and/or to combat the onset of senescence pigment blemishes comprising administering the extract of claim 8.

19. A method of combating skin aging, consisting of applying to skin the composition of claim 17.

20. A method of combating aggressions selected from the group consisting of sun, tobacco, pollution and stress consisting of applying to skin the composition of claim 17.

* * * * *